United States Patent [19]

Lover et al.

[11] 4,263,321
[45] Apr. 21, 1981

[54] ALKANOL AMIDE TOXICANTS

[75] Inventors: Myron J. Lover, Mountainside; Arnold J. Singer, South Orange; Donald M. Lynch, Waldwick; William E. Rhodes, III, Cranford, all of N.J.

[73] Assignee: Block Drug Company Inc., Jersey City, N.J.

[21] Appl. No.: 802,015

[22] Filed: May 31, 1977

[51] Int. Cl.³ ..................... A01N 37/18; A61K 31/16
[52] U.S. Cl. .................................................. 424/320
[58] Field of Search ........................................ 424/320

[56] References Cited

U.S. PATENT DOCUMENTS 3,626,011  12/1971  Bordenca et al. ............... 424/325 X

OTHER PUBLICATIONS

King, Chemicals Evaluated as Insecticides and Repellents at Orlando, Fla. May 1954, pp. 3–6, 216, 311.
D'Alelio et al., J.A.C.S. vol. 59 (1937) pp. 111–112.
Young, C. A. vol. 79 (1973) 35148n.

Primary Examiner—Allen J. Robinson
Attorney, Agent, or Firm—Ostrolenk, Faber, Gerb & Soffen

[57] ABSTRACT

Lower alkanol N-substituted fatty acid amides have been found to exhibit pediculicidal and/or ovicidal activity.

1 Claim, No Drawings

ALKANOL AMIDE TOXICANTS

BACKGROUND OF THE INVENTION

There are only a relatively few pediculicides which are commercially available today. The most popular pediculicidal toxicants are Lindane (gamma benzene hexachloride), Malathion [(S-1,2-dicarbethoxyethyl)-O,O-dimethyl phosphorodithioate], synergized pyrethrins and Cuprex (a combination of tetrahydronaphthalene, copper oleate and acetone, the acetone not asserted to be active). Because of increased concern about the overall safety of some of the known ectoparasitic toxicants, the search for new, safe and effective pediculicides has intensified recently.

Many species of insects encase their ova in protective sheaths which are impregnable to most toxicants. The "gestation" period of the egg is often relatively long in comparison to the life cycle of the adult forms. Thus, an agent effective only against adults must persist for the lifetime of the developing ovum or must be re-applied as successive hatching occur.

None of the pediculicidal toxicants in commercial use contribute to product performance, but must be supported by extraneous components for emulsifying, foaming or cleansing purposes.

Bordenca (U.S. Pat. No. 3,626,011) teaches that β-dialkylaminoalkyl ethers and thioethers of terpene alcohols are insecticidal or insectifugal to poultry lice.

It has now been found that lower alkanol N-substituted fatty acid amides exhibit pediculicidal and/or ovicidal activity. These compounds are known materials and have heretofore been used in shampoo formulations at concentrations of about 5% as conditioning agents and foaming agents.

It is the object of this invention to provide new safe and effective toxicants for lice and their ova. It is a further object of this invention to provide insect toxicants which have intrinsic emulsifying, foaming and cleansing properties. These may be used alone as primary active ingredients, or in combination with other toxicants where the alkanolamides contribute insecticidal power while providing valuable secondary properties to the compositions. This and other objects of the invention will become apparent to those skilled in the art from the following detailed description.

SUMMARY OF THE INVENTION

This invention relates to ectoparasiticidal toxicants and a method of controlling ectoparasites. More particularly, the invention relates to the use of lower alkanol N-substituted higher fatty acid amides as toxicants for lice and/or their ova and to toxicant compositions containing such amides as toxicants and adjunctives as emulsifiers, foaming agents and cleansers.

DESCRIPTION OF THE PREFERRED EMBODIMENTS

The toxicants of the instant invention are lower alkanol N-substituted fatty acid amides. The fatty acid amides can generally contain 10 to about 24 carbon atoms and preferably contain 12 to 18 carbon atoms. The amido nitrogen can be substituted by one or two of the lower alkanol groups, i.e., alkanol groups of 1 to 4 carbon atoms. Additionally, the alkanol groups need not be the same. Typical examples of lower alkanol N-substituted fatty acid amides of the instant invention include N-(2-hydroxypropyl) lauramide, N,N-bis-(2-hydroxyethyl) lauramide, N-(2-hydroxyethyl) cocamide, N,N-bis-(2-hydroxyethyl) cocamide, N,N-bis-(2-hydroxyethyl) mixed fatty acid amide and the like.

One or more of the toxic amides of the present invention can be incorporated into an active toxicant composition which can be in the form of a liquid, powder, lotion, cream, gel or aersol spray, or foam as the result of formulation with inert pharmaceutically acceptable carriers by procedures well known in the art. Of particular interest is the application to shampoo and body wash products, where all of the attributes of skin mildness, foaming propensities, detergency and insecticidal activity coalesce. Any pharmaceutically acceptable carrier, whether aqueous or not aqueous, which is inert to the active ingredient can be employed. By inert is meant that the carrier does not have a substantial detrimental effect on the pediculicidal or ovicidal toxicant activity of the active ingredient.

The active amides are incorporated into the toxicant composition used to treat the substrate (human or animal) in need of such treatment, believed to be in need of such treatment, or desired to be prophylactically protected in an effective toxicant amount. By such amount is meant the amount which will cause at least 50% of the ectoparasites exposed in the two minute immersion tests described below to die within 24 hours in the case of lice and within 2 weeks in case of the ova. The minimum concentration of amide required to provide an effective toxic amount varies considerably depending on the particular amides, the particular inert pharmaceutically acceptable carrier being employed and any other ingredients which are present. Thus, in one case a 10% concentration may suffice, while in other cases, concentrations as high as 25% may be required to obtain an effective toxic dose. Usually, the amides will be used in concentrations of about 5 to 25% and most preferably at concentrations of about 10 to 20%.

The instant amides can also be employed as an adjunct toxicant in a preparation which otherwise exhibits pediculicidal and/or ovicidal activity. In such preparations, the term "effective toxic dose" means that amount which will increase the mortality rate by at least about 20% in the standard immersion tests.

The two minute immersion tests referred to above is carried out as follows:

Pediculicidal activity: A 50 ml beaker is filled with tap water and allowed to come to room temperature (about 24° C.). Ten young adult male and ten young adult female lice (*Pediculus humanus corporis*) of the same age group and from the same stock colony are placed by a 2×2 cm coarse mesh path. The sample to be tested, maintained at room temperature, is shaken until homogeneous and placed into a 50 ml beaker. The mesh patch is placed into the sample immediately after pouring, allowed to submerge, and after two minutes is removed and immediately plunged into the beaker containing the tap water. The patch is vigorously agitated every ten seconds and after one minute the patch is removed and placed on paper toweling. The lice and then transferred to a 4×4 cm black corduroy cloth patch and this point of time is considered zero hours. Thereafter, the corduroy patch is placed in a petri dish which is covered and stored in a 30° C. holding chamber.

Ovicidal activity: 15 adult, 5 to 10 day old, female lice (*Pediculus humanus corporis*) are placed on a 2×2 cm nylon mesh patch which is placed in a petri dish, covered and maintained in an incubator at 30° C. for 24 hours. The adult lice are then removed and the number of plump, viable eggs and shriveled non-fertile eggs on the patch are recorded. The sample to be tested, maintained at room temperature, is shaken until homogeneous and poured into a 50 ml beaker. Immediately after the pouring, the mesh patch is placed into the beaker, allowed to submerge, and after two minutes is removed and immediately plunged into a 50 ml beaker containing tap water at room temperature (about 24° C.). The patch is vigorously agitated every ten seconds and after one minute, the patch is removed and placed on paper toweling for one minute. The patch is then placed in a petri dish which is covered and stored in the 30° C. incubator. Fourteen days following treatment, the number of hatched eggs and the number of shriveled or unhatched eggs is noted.

In both the pediculicidal and ovicidal two minute immersion tests, controls are run in identical manners to that described with room temperature (24° C.) tap water substituted for the sample to be tested. The results of the tests reported are net results.

The pediculicidal and ovicidal activity of various toxicants of the instant invention were tested in the two minute immersion test described above. The ratings set forth represent the percent mortality observed and the asterisks in the table indicate that the amide was a solid and could not be tested in undiluted form. The amides were evaluated in undiluted form (U.D.) or in a combination (C) containing 15 (w/w) percent amide, 25% isopropanol and 60% aqueous carrier.

| Compound | Pediculicidal Activity | | Ovicidal Activity | |
|---|---|---|---|---|
| | UD | C | UD | C |
| N-(2-hydroxypropyl) lauramide | * | 15 | * | 100 |
| N,N-bis(2-hydroxyethyl) lauramide | 100 | 15 | 100 | 0 |
| N-(2-hydroxyethyl) cocamide | * | 10 | * | 68 |
| N,N-bis-(2-hydroxyethyl) cocamide | 100 | 30 | 100 | 44 |
| N,N-bis-(2-hydroxyethyl) mixed fatty acid amide | 100 | 30 | 0 | 0 |

As noted above various end use formulations can be prepared. Some typical formulations are set forth below and the amounts recited are percentages by weight.

| Ovicidal Liquid suitable for mechanical spray for inunction | |
|---|---|
| Isopropyl alcohol | 25 |
| N-(2-hydroxypropyl) lauramide | 15 |
| Water | 60 |
| Ovicidal shampoo or skin wash | |
| Isopropyl alcohol | 25 |
| N-(2-hydroxypropyl) lauramide | 15 |
| Triethanolamine lauryl sulfate | 10 |
| Water | 50 |
| Pediculicidal and Ovicidal Powder | |
| N,N-bis-(2-hydroxyethyl) cocamide | 10 |
| Pyrophyllite | 90 |

Each of the foregoing typical formulations exhibit a pediculicidal or ovicidal rating of 100% mortality in the standard two minute immersion test.

Various changes and modifications can be made in the present invention without departing from the scope of the spirit thereof. The various embodiments which have been described above were set forth for illustration purposes only and were not intended to limit the invention. Unless otherwise specified, throughout this specification and claims, all temperatures have been in degrees Centigrade and all parts and percentages by weight.

We claim:

1. A method of controlling ectoparasites which comprises applying to a human or animal in need of such control, an effective toxic amount of N-(2-hydroxypropyl)lauramide.

* * * * *